US006689613B1

(12) United States Patent
Sun et al.

(10) Patent No.: US 6,689,613 B1
(45) Date of Patent: Feb. 10, 2004

(54) METHOD FOR PREPARING AND SCREENING CATALYSTS

(75) Inventors: Xiao-Dong Sun, Schenectady, NY (US); Navjot Singh, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/536,923

(22) Filed: Mar. 28, 2000

Related U.S. Application Data

(60) Provisional application No. 60/127,038, filed on Mar. 31, 1999.

(51) Int. Cl.$^7$ .................. G01N 31/10; G01N 33/53; G01N 33/20; B01J 21/18; C23C 16/32
(52) U.S. Cl. .................. 436/37; 435/7.1; 435/7.2; 435/DIG. 10; 435/DIG. 11; 435/DIG. 12; 435/DIG. 13; 436/501; 436/518; 436/82; 436/83; 436/84; 436/148; 436/149; 502/180; 502/181; 502/182; 502/183; 502/184; 502/185; 427/249.1
(58) Field of Search ... 435/7.1, 7.2, DIG. 10–DIG. 13; 436/501, 518, 37, 82–84, 148, 149; 502/180–185; 427/249.1

(56) References Cited

U.S. PATENT DOCUMENTS

| | | |
|---|---|---|
| 1,868,921 A | 7/1932 | Schmidt et al. |
| 4,014,933 A | 3/1977 | Boettger et al. |
| 4,153,581 A | 5/1979 | Haberemann |
| 4,497,788 A | 2/1985 | Bradley et al. |
| 4,518,575 A | 5/1985 | Porter et al. |
| 4,927,798 A | 5/1990 | Baldi |
| 4,929,737 A | 5/1990 | Lentz et al. |
| 4,970,123 A | 11/1990 | Witzke et al. |
| 5,124,075 A | 6/1992 | Yasuda et al. |
| 5,149,584 A | 9/1992 | Baker et al. |
| 5,165,909 A | 11/1992 | Tennent et al. |
| 5,171,560 A | 12/1992 | Tennent |
| 5,304,326 A | 4/1994 | Goto et al. |
| 5,500,200 A | 3/1996 | Mandeville et al. |
| 5,578,543 A | 11/1996 | Tennent et al. |
| 5,589,152 A | 12/1996 | Tennent et al. |
| 5,591,382 A | 1/1997 | Nahass et al. |
| 5,597,611 A | 1/1997 | Lennox et al. |
| 5,639,429 A | 6/1997 | Madronero delaCal |
| 5,643,990 A | 7/1997 | Uehara et al. |
| 5,650,370 A | 7/1997 | Tennent et al. |
| 5,707,916 A | 1/1998 | Snyder et al. |
| 5,726,116 A | 3/1998 | Moy et al. |
| 5,861,454 A | 1/1999 | Ikeda et al. |
| 5,985,356 A | 11/1999 | Schultz et al. |
| 6,004,617 A | 12/1999 | Schultz et al. |
| 6,518,218 B1 * | 2/2003 | Sun et al. .................. 502/259 |

FOREIGN PATENT DOCUMENTS

| | | |
|---|---|---|
| CA | 1155289 | 10/1983 |
| EP | 0424922 | 2/1991 |
| EP | 0564660 | 4/1993 |
| WO | 9007023 | 6/1990 |
| WO | 9304119 | 3/1993 |
| WO | 9710052 | 3/1997 |
| WO | 9847613 | 4/1998 |

OTHER PUBLICATIONS

"Formation and Texture of Carbon Nanofilaments by the Catalytic Decomposition of CO on Stainless–Steel Plate", S. Soneda, M. Makino, Carbon 38 (2000) 475–494.
"Electron Beam Studies of Individual Natural and Anthropogenic Microparticles: Compositions, Structures, and Surface Reactions", Peter R. Buseck and J.P. Bradley, Depts. of Chemistry and Geology, ArizontaState Univ., pp. 57–76 (1982).
"Peculiarities of Filamentous Carbon Formation in Methane Decomposition on Ni–Containing Catalysts", G.G. Kuvshinov, Y.I. Mogilnykh, D.G. Kuvshinov, V.I. Zaikovskii and L.B. Aveeva, Carbon vol. 36, Nos. 1–2, pp. 87–97, (1998).
"Carbon Single Wall Nanotubes Elaboration and Properties", P. Bernier, W. Maser, C. Journet, A. Loiseau, M. DeLaChapelle, S. Lefrant, R. Lee & J. Fischer, Carbon, vol. 36, No. 5, 6, pp. 675–680, (1998).
"High–Throughput Synthesis and Screening of Combinatorial Heterogeneous Catalyst Libraries", P. Cong et al., Angew. Chem. Int. Ed. 1999, 38, No. 4, pp. 484–488.
XP002058392—"Lenghts of Carbon Fibers Grown from Iron Catalyst Particles in Natural Gas", Gary G. Tibbetts, Journal of Crystal Growth 73 (1985) pp. 431–438.

* cited by examiner

*Primary Examiner*—Maurie Garcia Baker
(74) *Attorney, Agent, or Firm*—Andrew J. Caruso; Patrick K. Patnode

(57) ABSTRACT

A combinatorial method is provided for the preparation and screening of heterogeneous catalysts. The method comprises the steps of: (I) providing a library of elemental catalysts; (II) reacting the catalysts with a carbon source to form product directly on the catalyst; and (III) screening the products to evaluate the catalysts.

30 Claims, No Drawings

METHOD FOR PREPARING AND SCREENING CATALYSTS

CROSS REFERENCE TO RELATED APPLICATIONS

This application claims priority from Provisional Application No. 60/127,038 entitled "New Catalysts for Synthesis of Carbon Fibrils," filed on Mar. 31, 1999 which is incorporated herein by reference.

BACKGROUND OF THE INVENTION

The present invention is related to a method for preparing and screening catalysts. In particular, the present invention is related to a combinatorial method for preparing and screening catalysts.

Combinatorial methods have been used extensively in the pharmaceutical industry. These methods can be an efficient and rapid way to synthesize and screen numerous different substances on a microscale. Combinatorial methods represent a systematic way to screen for potential drugs, catalysts and materials. Due to the miniaturization of the reaction with combinatorial chemistry, there are typically problems in translating reaction conditions and parameters from a microscale reaction to a corresponding macroscale reaction.

Heterogeneous catalysts have been found to be particularly useful in solid state reactions. In particular, metal alloys and elemental metals are used as heterogeneous catalysts to synthesize a variety of materials. However, most metal alloys and elemental metals are prone to oxidation. Thus, methods used to synthesize catalysts from metal alloys and elemental metals must be practiced in a controlled environment.

A multitude of combinations of metal alloys and elemental metals may be used to form catalysts. Therefore, the study of potential catalysts in the vast array of metal alloys and elemental metals may be a slow and tedious process. Due to the inefficiency of typical methods, new methods to discover catalysts are constantly being sought.

BRIEF SUMMARY OF THE INVENTION

The present invention provides a combinatorial method for the preparation and screening of catalysts. In an exemplary embodiment, the method includes the steps of:

(I) providing a library of elemental catalysts;

(II) reacting the catalysts with a carbon source to form product directly on the catalyst; and (III) screening the products to evaluate the catalysts.

DETAILED DESCRIPTION OF THE INVENTION

A combinatorial method has been discovered which enables rapid synthesis and screening of catalysts. The combinatorial method for the discovery of catalysts is a microscale reaction. The miniaturization of the reaction enables virtually any number of different catalysts to be screened at once making it an efficient method for discovery of new catalysts. The small scale of the reaction can have environmental benefits due to the amount of chemicals used which is usually in units of micrograms. It is both a faster and a cleaner way to do experiments in search of catalysts. "Catalysts" as used herein refer to elemental metals, metal alloys, or combinations thereof which are effective at catalytic levels for converting a reactive substrate to a product. In particular, the combinatorial method is used for discovering catalysts used for making carbon fibrils by a heterogeneously catalyzed process.

Carbon fibrils are microscopic fibers of carbon typically having a diameter in a range between about 1 nanometer and about 500 nanometers. In particular, it is preferable to synthesize carbon fibrils with a diameter in a range between about 10 nanometers and about 50 nanometers. The aspect ratio of length of the carbon fibril to the diameter of the carbon fibril is typically greater than about 100.

Combinatorial methods used for synthesizing catalysts for carbon fibril formation include a thin film catalysts library and a powder catalysts library. "Library" as used herein refers to two or more different catalysts placed on a substrate. The catalysts may be deposited on the substrate sequentially or preferably, simultaneously. "Substrate" as used herein refers to any material which supports a large collection of catalysts. There is typically a minimum interaction between the supported catalysts and substrate material during chemical reaction or synthesis. However, certain substrates which have been found to be catalytic substances may have a synergistic effect on the production of carbon fibrils. Typical substrates include ceramics, for example, alumina; glass; metals, for example, aluminum, stainless steel, copper, silver, gold, platinum, and brass; and single crystals, for example, quartz, magnesium oxide, silicon, sapphire, and lanthanum aluminate.

In a preferred embodiment, a thin film catalysts library is produced using a multiple gun sputtering deposition system. The multiple gun sputtering deposition system contains elemental metal or metal alloy source placed in each gun cavity. An electrical discharge can be created at each source by applying radio frequency (RF) or direct current (DC) power in a range between about 10 Watts and about 1,000 Watts through the sputter gun, which heats the elemental metal or metal alloy to form a metal plasma vapor. The metal vapor from the sputter gun is deposited onto the counter-facing substrate. The rate of the material deposition is dependent on the level of power input. The amount of material deposited can be altered by changing the amount of time the sputter gun is powered. By coupling thin film deposition from different sputter guns with different masking patterns from an array of deposition masks, a matrix library of thin film catalysts is created. Due to the multiplicity of the number of guns and hence, elemental metals and metal alloys which can be used, the possible compositions and stoichiometry of metals which are deposited on the substrate are countless thus allowing for exploration of a vast experimental space. With multiple sputtering guns, any combination of metals can be deposited on a substrate to form a thin film catalysts library.

In various embodiments, the thin film catalysts library is built with an in-vacuum feed-in system. This enables the metal alloy library to be made without breaking the vacuum to change sources and masks for the next deposition, which keeps the metals in an atmospherically controlled environment. In particular, the in-vacuum feed-in system is filled with a gas, for example, argon, helium, nitrogen, hydrogen, and mixtures thereof. The gas in the thin film catalysts library is hereinafter referred to as "sputtering gas". The in-vacuum feed-in system increases the speed in the generation of libraries, and also prevents the formation of metal oxides from elemental metals and alloys which are sensitive to oxygen. Typically, the prevention of oxidation of the elemental metals and alloys is a concern but the in-vacuum feed-in system substantially inhibits the oxidation of metals and metal alloys.

Once the metal vapors are deposited on the substrate, the thin film catalysts library is typically thermally annealed.

The library is heated to a temperature in a range between about 200° C. and about 1100° C., and preferably, to a temperature in a range between about 600° C. and about 800° C. The library is also typically in a non-organic gas environment to substantially prevent the oxidation of the elemental metals or metal alloys. Examples of typical gases include argon, helium, nitrogen, hydrogen and mixtures thereof. Although the invention is not dependent on theory, it is believed that the temperature and atmospheric conditions promote the interdiffusion of the combined metals to form catalysts.

An alternative manner for creating a catalysts library is through the use of a multiple channel liquid dispensing system. Each of an array of liquid dispensers can be individually controlled and programmed to dispense a liquid material. In preferred embodiments, the liquid dispensers are each filled with a soluble metal precursor such as a nitrate, acetate, or other aqueous soluble metal salt compound. An elemental metal, metal alloy or mixture thereof is carried in a soluble precursor. Once the soluble precursor or combination of soluble precursors comprising the elemental metal, metal alloy or combination thereof is deposited on the substrate as a liquid, the library is typically dried, calcined in air, and annealed in nitrogen, argon, helium, hydrogen, or combinations thereof to form an oxide-containing powder catalyst library. To synthesize metal or alloy materials from such oxide-containing powders, reducing (for example, using hydrogen, charcoal, or carbon monoxide) in a time range between about 0.5 hours and about 12 hours at a temperature in a range between about 300° C. and about 800° C. is found to be sufficient for most miniaturized samples in the library. By use of the soluble precursor, the oxidation of any elemental metal or alloy is not a problem.

Once the catalysts are formed, the library is placed in a suitable reactor, such as a chemical vapor deposition reactor. Typically, the catalysts on the substrate are placed in a reaction chamber, such as a fixed bed quartz tube reactor, at a temperature in a range between about 300° C. and about 1000° C., and preferably in a range between about 400° C. and about 700° C. Commonly, the reactor is initially filled with a non-organic gas in order to create a non-reactive atmosphere in the reaction chamber. In particular, the reactor is filled with a non-organic gas in order to create a non-oxidative environment such that the metal catalysts will not be oxidized. Typically, argon gas and hydrogen gas are used and are present in a volume ratio in a range between about 5.5:1 and about 1:1. A mixture of argon and hydrogen is most commonly used at a volume ratio of about 5:1 argon to hydrogen. When the organic vapor or reactant product of the organic vapor and non-organic gas under the process conditions come in contact with the catalysts, carbon fibrils may be synthesized. Due to the varying volume capacity of different reaction chambers, the flow rate can vary. Typically, the flow rate of the gas is such that it takes approximately 8 minutes to refresh the gas in the tube.

The reactor can be operated under a pressure in a range between about 1 torr and about 100 atmospheres. The synthesis is typically run at a pressure in a range between about 100 torr and about 10 atmospheres.

A carbon source (e.g., organic vapor) is released in the reactor and product, such as carbon fibrils, is formed directly on the library. Examples of organic vapors typically used in a chemical vapor deposition reactor include acetylene, ethylene, methane, benzene, carbon monoxide or mixtures thereof. Commonly, the organic vapor is mixed with one of the gases used to create a non-oxidative environment as mentioned above. Typically, a combination of ethylene gas with hydrogen gas is used at a volume ratio of 5:1. The flow rate of the vapor is such that it takes approximately 8 minutes to refresh the vapor in the tube. Carbon fibrils may also be synthesized by the reactant product of the gas and the organic vapor thereof under the process conditions. The formation of the product directly on the catalyst surface automatically accelerates the process of discovering catalysts. In addition, all the samples are integrated on the same library and may be simultaneously analyzed.

Screening for identity of product and efficiency of product formation can be done in several different ways. Examples include optical microscopy, electron microscopy, such as transmission electron microscopy and scanning electron microscopy, laser profilometry, X-ray diffraction, Raman scattering and high throughput x-ray diffraction. In particular, scanning electron microscopy is useful since yield and morphology may be assessed to identify promising catalysts.

By using combinatorial methods to discover heterogeneous catalysts, the rate of discovery compared to conventional methods may be orders of magnitude faster. Instead of examining each catalyst independently, a multitude of catalysts can be examined simultaneously. In addition, the controlled environment in which the catalysts are made ensures that the metals, metal alloys, and combinations thereof are not oxidized and the desired product can be obtained.

In order that those skilled in the art will be better able to practice the invention, the following examples are given by way of illustration and not by way of limitation.

EXAMPLE 1

A 128-membered thin film catalysts library was fabricated with four metals: iron, nickel, molybdenum, and chromium on a quartz substrate (2.54 centimeters×2.54 centimeters× 0.5 millimeters) using an in-vacuum multiple gun sputtering deposition system with high purity (greater than 99.9%) argon as the sputtering gas. The catalysts were annealed at 200° C. for greater than 24 hours in a vacuum oven at a pressure around 10 torr. The library was then loaded into a chemical vapor deposition reactor which was free of any volatile materials, pumped to high vacuum (less than about 1 torr) and the reactor was flushed with a mixture of high purity (greater than 99.9%) hydrogen and high purity argon wherein the argon and hydrogen were in a volume ratio of about 5:1. The flow rate was such that it took about 8 minutes to refresh the gas in the tube. The temperature was slowly ramped up from room temperature to 500° C. and held at this temperature for about 12 hours before ramping up to a temperature of 600° C. at 2° C. per minute under the same gas flow. After further conditioning at 600° C. for an hour, the argon was switched off and replaced with a flow of ethylene. The volume ratio of ethylene to hydrogen was about 5:1. The library of catalysts was reacted for a half hour before the ethylene source was shut off and replaced with argon. Under a constant flow of argon and hydrogen, the furnace was then turned off and allowed to cool to room temperature before the library was taken out for analysis.

The thin film catalysts library was observed under a reflective optical microscope for the primary screen of catalyst candidates. Subsequently, scanning electron microscopy was used for secondary screening focusing on sample sites with adequate amount of carbon product. The following catalysts were shown to produce carbon fibrils by primary and secondary screening of the catalysts candidates: nickel and molybdenum; nickel and chromium; nickel, molybdenum and chromium; iron, nickel, and chromium; iron, nickel and molybdenum; and iron, nickel, molybdenum, and chromium.

EXAMPLE 2

A 128-membered powder catalysts library was fabricated with six metals: iron, cobalt, aluminum, zinc, chromium, and yttrium on a quartz substrate (2.54 centimeters×2.54 centimeters×0.5 millimeters) as seen in Table 1. Solutions of high purity metal nitrates (one molar in concentration) were used as metal precursors. Once the powder catalysts library was fabricated, the heterogeneous catalysts were annealed at 200° C. for greater than 24 hours in a vacuum oven (pressure about 10 torr). The library was then loaded into a chemical vapor deposition reactor which was free of any volatile materials, pumped to high vacuum (less than 1 torr), and the reactor was flushed with a mixture of high purity (greater than 99.9%) hydrogen and high purity (greater than 99.9%) argon into the tube wherein the argon to hydrogen volume ratio was about 5:1. The flow rate was such that it took about 8 minutes to refresh the gas in the tube. The temperature was slowly ramped up from room temperature to 500° C. The catalysts library was annealed for about 12 hours before ramping up the temperature to 600° C. at 2° C. per minute, under the same gas flow. After further annealing at a temperature of 600° C. for an hour, the argon was switched off and replaced with a flow of ethylene. The volume ratio of ethylene to hydrogen was about 5:1. The library of catalyst candidates was reacted for about 30 minutes before the ethylene source was shut off and replaced with argon. Under a constant flow of argon and hydrogen, the furnace was then turned off and allowed to cool to room temperature before the library was taken out for evaluation.

The powder library was observed under a reflective optical microscope for the primary screen of catalyst candidates. A secondary screen was made using scanning electron microscopy (SEM) focusing on sample sites with adequate amount of carbon product. The following catalysts were determined as catalysts which produced carbon fibrils: nickel and iron; cobalt and iron; chromium and cobalt; zinc and cobalt; nickel and cobalt; nickel and chromium; nickel and zinc; nickel and copper; cobalt and copper; and nickel and aluminum.

TABLE 1

| Fe4Fe2 | Co4Fe2 | Ni4Fe2 | Cr4Fe2 | Zn4Fe2 | Y4Fe2 | Cu4Fe2 | Al4Fe2 |
|---|---|---|---|---|---|---|---|
| Fe4Co2 | Co4Co2 | Ni4Co2 | Cr4Co2 | Zn4Co2 | Y4Co2 | Cu4Co2 | Al4Co2 |
| Fe4Ni2 | Co4Ni2 | Ni4Ni2 | Cr4Ni2 | Zn4Ni2 | Y4Ni2 | Cu4Ni2 | Al4Ni2 |
| Fe4Cr2 | Co4Cr2 | Ni4Cr2 | Cr4Cr2 | Zn4Cr2 | Y4Cr2 | Cu4Cr2 | Al4Cr2 |
| Fe4Zn2 | Co4Zn2 | Ni4Zn2 | Cr4Zn2 | Zn4Zn2 | Y4Zn2 | Cu4Zn2 | Al4Zn2 |
| Fe4Y2 | Co4Y2 | Ni4Y2 | Cr4Y2 | Zn4Y2 | Y4Y2 | Cu4Y2 | Al4Y2 |
| Fe4Cu2 | Co4Cu2 | Ni4Cu2 | Cr4Cu2 | Zn4Cu2 | Y4Cu2 | Cu4Cu2 | Al4Cu2 |
| Fe4Al2 | Co4Al2 | Ni4Al2 | Cr4Al2 | Al4Al2 | Y4Al2 | Cr4Al2 | Al4Al2 |
| Fe5Fe | Co5Fe | Ni5Fe | Cr5Fe | Zn5Fe | Y5Fe | Cu5Fe | Al5Fe |
| Fe5Co | Co5Co | Ni5Co | Cr5Co | Zn5Co | Y5Co | Cu5Co | Al5Co |
| Fe5Ni | Co5Ni | Ni5Ni | Cr5Ni | Zn5Ni | Y5Ni | Cu5Ni | Al5Ni |
| Fe5Cr | Co5Cr | Ni5Cr | Cr5Cr | Zn5Cr | Y5Cr | Cu5Cr | Al5Cr |
| Fe5Zn | Co5Zn | Ni5Zn | Cr5Zn | Zn5Zn | Y5Zn | Cu5Zn | Al5Zn |
| Fe5Y | Co5Y | Ni5Y | Cr5Y | Zn5Y | Y5Y | Cu5Y | Al5Y |
| Fe5Cu | Co5Cu | Ni5Cu | Cr5Cu | Zn5Cu | Y5Cu | Cu5Cu | Al5Cu |
| Fe5Al | Co5Al | Ni5Al | Cr5Al | Al5Al | Y5Al | Cu5Al | Al5Al |

The ratios of the metals are molar.

EXAMPLE 3

Using the method of Example 2, a 128-membered powder catalysts library was fabricated with eight metals: copper, iron, zinc, nickel, aluminum, cobalt, yttrium, and chromium on a quartz substrate (2.54 centimeters×2.54 centimeters×0.5 millimeters) as seen in Table 2. The following catalysts were shown to produce carbon fibrils: copper and iron; and aluminum and cobalt.

TABLE 2

| Cu1.44Fe0.14 | Cu1.34Fe0.24 | Cu1.24Fe0.34 | Cu1.14Fe0.44 |
|---|---|---|---|
| Cu1.4Fe0.18 | Cu1.3Fe0.28 | Cu1.2Fe0.38 | Cu1.1Fe0.48 |
| Zn1.36Ni0.22 | Zn1.26Ni0.32 | Zn1.16Ni0.42 | Zn1.06Ni0.52 |
| Zn1.32Ni0.26 | Zn1.22Ni0.36 | Zn1.12Ni0.46 | Zn1.02Ni0.56 |
| Al1.28Co0.3 | Al1.18Co0.4 | Al1.08Co0.5 | Al0.98Co0.6 |
| Al1.24Co0.34 | Al1.14Co0.44 | Al1.04Co0.54 | Al0.94Co0.64 |
| Y1.2Cr0.38 | Y1.1Cr0.48 | Y1Cr0.58 | Y0.9Cr0.68 |
| Y1.16Cr0.42 | Y1.06Cr0.52 | Y0.96Cr0.62 | Y0.86Cr0.72 |
| Cr1.12Y0.46 | Cr1.02Y0.56 | Cr0.92Y0.66 | Cr0.82Y0.76 |
| Cr1.08Y0.5 | Cr0.98Y0.6 | Cr0.88Y0.7 | Cr0.78Y0.8 |
| Co1.04Al0.54 | Co0.94Al0.64 | Co0.84Al0.74 | Co0.74Al0.84 |
| Co1Al0.58 | Co0.9Al0.68 | Co0.8Al0.78 | Co0.7Al0.88 |
| Ni0.96Zn0.62 | Ni0.86Zn0.72 | Ni0.76Zn0.82 | Ni0.66Zn0.92 |
| Ni0.92Zn0.66 | Ni0.82Zn0.76 | Ni0.72Zn0.86 | Ni0.62Zn0.96 |
| Fe0.88Cu0.7 | Fe0.78Cu0.8 | Fe0.68Cu0.9 | Fe0.58Cu1 |
| Fe0.84Cu0.74 | Fe0.74Cu0.84 | Fe0.64Cu0.94 | Fe0.54Cu1.04 |
| Cu1.04Fe0.54 | Cu0.94Fe0.64 | Cu0.84Fe0.74 | Cu0.74Fe0.84 |
| Cu1Fe0.58 | Cu0.9Fe0.68 | Cu0.8Fe0.78 | Cu0.7Fe0.88 |
| Zn0.96Ni0.62 | Zn0.86Ni0.72 | Zn0.76Ni0.82 | Zn0.66Ni0.92 |
| Zn0.92Ni0.66 | Zn0.82Ni0.76 | Zr0.72Ni0.86 | Zn0.62Ni0.96 |
| Al0.88Co0.7 | Al0.78Co0.8 | Al0.68Co0.9 | Al0.58Co1 |
| Al0.84Co0.74 | Al0.74Co0.84 | Al0.64Co0.94 | Al0.54Co1.04 |
| Y0.8Cr0.7B | Y0.7Cr0.88 | Y0.6Cr0.98 | Y0.5Cr1.08 |
| Y0.76Cr0.82 | Y0.66Cr0.92 | Y0.56Cr1.02 | Y0.46Cr1.12 |
| Cr0.72Y0.86 | Cr0.62Y0.96 | Cr0.52Y1.06 | Cr0.42Y1.16 |
| Cr0.68Y0.9 | Cr0.58Y1 | Cr0.48Y1.1 | Cr0.38Y1.2 |
| Co0.64Al0.94 | Co0.54Al1.04 | Co0.44Al1.14 | Co0.34Al1.24 |
| Co0.6Al0.98 | Co0.5Al1.08 | Co0.4Al1.18 | Co0.3Al1.28 |
| Ni0.56Zn1.02 | Ni0.46Zn1.12 | Ni0.36Zn1.22 | Ni0.26Zn1.32 |
| Ni0.52Zn1.06 | Ni0.42Zn1.16 | Ni0.32Zn1.26 | Ni0.22Zn1.36 |
| Fe0.48Cu1.1 | Fe0.3BCu1.2 | Fe0.28Cu1.3 | Fe0.18Cu1.4 |
| Fe0.44Cu1.14 | Fe0.34Cu1.24 | Fe0.24Cu1.34 | Fe0.14Cu1.44 |

* The ratios of the metals are molar.

EXAMPLE 4

Using the method of Example 2, a 128-membered powder library was fabricated with eight metals: copper, iron, zinc, nickel, aluminum, cobalt, yttrium, and chromium on a quartz substrate (2.54 centimeters×2.54 centimeters×0.5 millimeters) as seen in Table 3. The following catalysts produced carbon fibrils: cobalt, iron and copper; nickel, iron and yttrium; copper, iron, cobalt, and aluminum; cobalt and copper; zinc, cobalt, chromium, and copper; yttrium, cobalt, nickel, and copper; cobalt, nickel and copper; nickel, chromium, and yttrium; cobalt, zinc and copper; zinc, yttrium, chromium, and nickel; aluminum, iron, and nickel;

nickel, iron, yttrium, and aluminum; nickel, cobalt, and copper; chromium and zinc; nickel and yttrium; and chromium, aluminum, and iron.

TABLE 3

| | | | |
|---|---|---|---|
| Fe4Fe2Al5 | Co4Fe2Cu5 | Ni4Fe2Y5 | Cr4Fe2Zn5 |
| Fe4Co2Al5 | Co4Co2Cu5 | Ni4Co2Y5 | Cr4Co2Zn5 |
| Fe4Ni2Al5 | Co4Ni2Cu5 | Ni4Ni2Y5 | Cr4Ni2Zn5 |
| Fe4Cr2Al5 | Co4Cr2Cu5 | Ni4Cr2Y5 | Cr4Cr2Zn5 |
| Fe4Zn2Al5 | Co4Zn2Cu5 | Ni4Zn2Y5 | Cr4Zn2Zn5 |
| Fe4Y2Al5 | Co4Y2Cu5 | Ni4Y2Y5 | Cr4Y2Zn5 |
| Fe4Cu2Al5 | Co4Cu2Cu5 | Ni4Cu2Y5 | Cr4Cu2Zn5 |
| Fe4Al2Al5 | Co4Al2Cu5 | Ni4Al2Y5 | Cr4Al2Al5 |
| Zn4Fe2Cr5 | Y4Fe2Ni5 | Cu4Fe2Co5 | Al4Fe2Fe5 |
| Zn4Co2Cr5 | Y4Co2Ni5 | Cu4Co2Co5 | Al4Co2Fe5 |
| Zn4Ni2Cr5 | Y4Ni2Ni5 | Cu4Ni2Co5 | Al4Ni2Fe5 |
| Zn4Cr2Cr5 | Y4Cr2Ni5 | Cu4Cr2Co5 | Al4Cr2Fe5 |
| Zn4Zn2Cr5 | Y4Zr2Ni5 | Cu4Zn2Co5 | Al4Zn2Fe5 |
| Zn4Y2Cr5 | Y4Y2Ni5 | Cu4Y2Co5 | Al4Y2Fe5 |
| Zn4Cu2Cr5 | Y4Cu2Ni5 | Cu4Cu2Co5 | Al4Cu2Fe5 |
| Zn5FeCr2.5Al2.5 | Y5FeNi2.5Al2.5 | Cu5FeCo2.5Al2.5 | Al5FeFe2.5Al2.5 |
| Zn5CoCr2.5Cu2.5 | Y5CoNi2.5Cu2.5 | Cu5CoCo2.5Cu2.5 | Al5CoFe2:5Cu2.5 |
| Zn5NiCr2.5Y2.5 | Y5NiNi2.5Y2.5 | Cu5NiCo2.5Y2.5 | Al5NiFe2.5Y2.5 |
| Zn5CrCr2.5Zn2.5 | Y5CrNi2.5Zn2.5 | Cu5CrCo2.5Zn2.5 | Al5CrFe2.5Zn2.5 |
| Zn5ZnCr2.5Cr2.5 | Y5ZnNi2.5Cr2.5 | Cu5ZnCo2.5Cr2.5 | Al5ZnFe2.5Cr2.5 |
| Zn5YCr2.5Ni2.5 | Y5YNi2.5Ni2.5 | Cu5YCo2.5Ni2.5 | Al5YFe2.5Ni2.5 |
| Zn5CuCr2.5Co2.5 | Y5CuNi2.5Co2.5 | Cu5CuCo2.5Co2.5 | Al5CuFe2.5Co2.5 |
| Al5AlCr2.5Fe2.5 | Y5AlNi2.5Fe2.5 | Cu5AlCo2.5Fe2.5 | Al5AlFe2.5Fe2.5 |
| Fe5FeAl2.5Al2.5 | Co5FeCu2.5Al2.5 | Ni5FeY2.5Al2.5 | Cr5FeZn2.5Al2.5 |
| Fe5CoAl2.5Cu2.5 | Co5CoCu2.5Cu2.5 | Ni5CoY2.5Cu2.5 | Cr5CoZn2.5Cu2.5 |
| Fe5NiAl2.5Y2.5 | Co5NiCu2.5Y2.5 | Ni5NiY2.5Y2.5 | Cr5NiZn2.5Y2.5 |
| Fe5CrAl2.5Zn2.5 | Co5CrCu2.5Zn2.5 | Ni5CrY2.5Zn2.5 | Cr5CrZn2.5Zn2.5 |
| Fe5ZnAl2.5Cr2.5 | Co5ZnCu2.5Cr2.5 | Ni5ZnY2.5Cr2.5 | Cr5ZnZn2.5Cr2.5 |
| Fe5YAl2.5Ni2.5 | Co5YCu2.5Ni2.5 | Ni5YY2.5Ni2.5 | Cr5YZn2.5Ni2.5 |
| Fe5CuAl2.5Co2.5 | Co5CuCu2.5Co2.5 | Ni5CuY2.5Co2.5 | Cr5CuZn2.5Co2.5 |
| Fe5AlAl2.5Fe2.5 | Co5AlCu2.5Fe2.5 | Ni5AlY2.5Fe2.5 | CrsAlAl2.5Fe2.5 |
| Al4Al2Cr5 | Y4Al2Ni5 | Co4Al2Co5 | Al4Al2Fe5 |

The ratios of the metals are molar.

It is evident that with the vast array of elemental metals and metal alloys, multiple catalysts can be fabricated and screened concurrently. The combinatorial method enables rapid discovery of the few catalysts which successfully produce carbon fibrils in an array of combinations of metals and metal alloys which do not produce carbon fibrils under the processing conditions. For instance, it was unexpectedly found that some iron combinations were ineffective catalysts for the production of carbon fibrils. Once catalysts have been determined, the catalysts can be produced on a macroscale.

While typical embodiments have been set forth for the purpose of illustration, the foregoing descriptions should not be deemed to be a limitation on the scope of the invention. Accordingly, various modifications, adaptations, and alternatives may occur to one skilled in the art without departing from the spirit and scope of the present invention as defined by the following claims.

What is claimed is:

1. A combinatorial method for the preparation and screening of catalysts, said method comprising the steps of:
   (I) providing a library of elemental catalysts, wherein said catalysts comprise aluminum metal;
   (II) reacting the catalysts with a carbon source to form product directly on the catalyst; and
   (III) screening the products to evaluate the catalysts for carbon fibrils.

2. A combinatorial method for the preparation and screening of catalysts, said method comprising the steps of:
   (I) providing a library of elemental catalysts, wherein said catalysts comprise aluminum metal;
   (II) reacting the catalysts with a carbon source to form product directly on the catalysts; and
   (III) screening the products via microscopy to evaluate the catalysts for carbon fibrils.

3. The method in accordance with claim 1, wherein step I is carried out utilizing an in-vacuum multiple gun sputtering deposition system.

4. The method in accordance with claim 1, wherein step II occurs at a temperature in a range between about 200° C. and about 1100° C.

5. The method in accordance with claim 4, wherein step II occurs at a temperature in a range between about 600° C. and about 800° C.

6. The method in accordance with claim 1, wherein the carbon source comprises acetylene, ethylene, methane, benzene, carbon monoxide or a mixture thereof.

7. The method in accordance with claim 1, wherein step II occurs at a temperature in a range between about 300° C. and about 1000° C.

8. The method in accordance with claim 7, wherein step II occurs at a temperature in a range between about 400° C. and about 700° C.

9. The method in accordance with claim 1, wherein step I includes depositing a library of catalysts on a substrate to form a library of elemental catalysts wherein said catalysts comprise aluminum metal.

10. The method in accordance with claim 1, wherein step I includes annealing the catalysts.

11. A combinatorial method for the preparation and screening of catalysts for making carbon fibrils, said method comprising the steps of:
   (I) depositing a library of catalysts on a substrate to form a library of elemental catalysts wherein said catalysts comprise aluminum metal alloys;
   (II) annealing the catalysts;
   (III) reacting the catalysts in a chemical vapor deposition reactor to form carbon fibrils directly on the catalyst; and (IV) screening the carbon fibrils directly on the library to evaluate the catalysts.

12. The method of claim 11, wherein step III comprises contacting the catalysts with a carbon source.

13. The method in accordance with claim 12, wherein step III is carried out in the presence of a non-organic gas.

14. The method in accordance with claim 13, wherein the non-organic gas comprises argon, helium, nitrogen, hydrogen or a mixture thereof.

15. The method in accordance with claim 12, wherein the carbon source comprises acetylene, ethylene, methane, benzene, carbon monoxide or a mixture thereof.

16. The method in accordance with claim 11, wherein step II occurs at a temperature in a range between about 200° C. and about 1100° C.

17. The method in accordance with claim 16, wherein step II occurs at a temperature in a range between about 600° C. and about 800° C.

18. The method in accordance with claim 11, wherein step III occurs at a temperature in a range between about 300° C. and about 1000° C.

19. The method in accordance with claim 18, wherein step III occurs at a temperature in a range between about 400° C. and about 700° C.

20. A combinatorial method for the preparation and screening of catalysts for making carbon fibrils, said method comprising the steps of:

(I) depositing a library of catalysts on a substrate wherein said catalysts comprise aluminum alloys;

(II) annealing the catalysts;

(III) reacting the catalysts in a chemical vapor deposition reactor in the presence of a gas comprising argon, hydrogen or combinations thereof and an organic vapor comprising acetylene, ethylene or a mixture thereof to form carbon fibrils directly on the catalysts; and (IV) screening the carbon fibrils directly on the library to evaluate the catalysts.

21. The method in accordance with claim 20, wherein step II occurs at a temperature in a range between about 600° C. and about 800° C.

22. The method in accordance with claim 20, wherein step III occurs at a temperature in a range between about 400° C. and about 700° C.

23. The method in accordance with claim 2, wherein step I is carried out utilizing an in-vacuum multiple gun sputtering deposition system.

24. The method in accordance with claim 2, wherein step II occurs at a temperature in a range between about 200° C. and about 1100° C.

25. The method in accordance with claim 24, wherein step II occurs at a temperature in a range between about 600° C. and about 800° C.

26. The method in accordance with claim 2, wherein the carbon source comprises acetylene, ethylene, methane, benzene, carbon monoxide or a mixture thereof.

27. The method in accordance with claim 2, wherein step II occurs at a temperature in a range between about 300° C. and about 1000° C.

28. The method in accordance with claim 27, wherein step II occurs at a temperature in a range between about 400° C. and about 700° C.

29. The method in accordance with claim 2, wherein step I includes depositing a library of catalysts on a substrate to form a library of elemental catalysts wherein said catalysts comprise aluminum metal.

30. The method in accordance with claim 2, wherein step I includes annealing the catalysts.

* * * * *